United States Patent [19]

Lyon et al.

[11] Patent Number: 5,531,106
[45] Date of Patent: Jul. 2, 1996

[54] VOLUME CONTROL SYSTEM FOR A CHROMATOGRAPH

[76] Inventors: Dan Lyon, 173 Plattekill-Ardonia Rd., Wallkill, N.Y. 12589; Terrance Perrone, 653 Bridge St., Hopewell Junction, N.Y. 12533; Joseph Rutz, 79 Rombout Ave., Beacon, N.Y. 12508

[21] Appl. No.: 375,420

[22] Filed: Jan. 18, 1995

[51] Int. Cl.⁶ .................................................. G01N 30/00
[52] U.S. Cl. ...................... 73/61.560; 422/70; 436/161; 210/656
[58] Field of Search ..................... 73/61.56, 863.02, 73/863.03, 863.83, 864.34; 210/656, 198.2; 422/70; 436/161

[56] References Cited

U.S. PATENT DOCUMENTS

| | | |
|---|---|---|
| 3,975,946 | 8/1976 | Ball et al. . |
| 4,073,725 | 2/1978 | Takeuchi et al. ............... 210/198.2 |
| 4,102,782 | 7/1978 | Saito et al. . |
| 4,181,022 | 1/1980 | Perry ............................. 73/863.83 |
| 4,366,060 | 12/1982 | Leiser et al. ................... 210/198.2 |
| 4,382,000 | 5/1983 | Wisebaker et al. . |
| 4,384,958 | 5/1983 | Wisebaker et al. . |
| 4,478,713 | 10/1984 | Girot et al. .................... 210/198.2 |
| 4,629,561 | 12/1986 | Shirato et al. . |
| 4,698,151 | 10/1987 | Ozawa et al. .................. 210/198.2 |
| 4,861,555 | 8/1989 | Mowery, Jr. . |
| 4,942,018 | 7/1990 | Munk ............................. 422/70 |
| 4,969,993 | 11/1990 | Nash, Jr. et al. . |
| 4,991,428 | 2/1991 | Heyde . |
| 5,042,293 | 8/1991 | Heyde . |
| 5,118,628 | 6/1992 | Krumpen et al. ............... 422/70 |
| 5,277,871 | 1/1994 | Fujii et al. . |
| 5,286,652 | 2/1994 | James et al. . |
| 5,389,251 | 2/1995 | Del Mar ......................... 210/198.2 |

FOREIGN PATENT DOCUMENTS

| | | | |
|---|---|---|---|
| 477811 | 4/1992 | European Pat. Off. ............. | 73/61.56 |
| 1260856 | 9/1986 | U.S.S.R. ............................. | 73/61.56 |

*Primary Examiner*—Hezron E. Williams
*Assistant Examiner*—Daniel S. Larkin
*Attorney, Agent, or Firm*—McAulay Fisher Nissen Goldberg & Kiel

[57] ABSTRACT

A sample apparatus for a chromatogram utilizes a calibrated sample holding device such as a burette, having a liquid level sensor located at a selected height on the sample holding device. A pump is provided for transporting liquid to the sample holding device. A switch, which may be integrated with the liquid level sensor, connected to the pump such that when the selected liquid level is reached, the switch halts the flow of liquid to the sample holding device. Optionally, a second transport device provided for discharging the sample, with the second transport device utilizing an outlet valve responsive to a signal from a controller such that the sample holding device can be cyclically filled and emptied, in a sequence satisfactory to efficient operation of the chromatograph. Utilizing the apparatus of the invention, precise volumetric samples can be delivered to the device, to assure consistent analytical results from sample to sample.

11 Claims, 3 Drawing Sheets

VOLUME CONTROL SYSTEM FOR A CHROMATOGRAPH

TECHNICAL FIELD

This invention relates to a chromatograph and more particularly to a method and apparatus for precise volume control of a plurality of submitted sequentially samples to the chromatograph for analysis.

BACKGROUND

Chromatography is a procedure used for analyzing a sample to identify one or more of its constituents. The procedure for analysis involves passing a sample of the material to be analyzed through a body of material and detecting the relative separation of various sample constituents. One particular type of chromatograph is an ion chromatograph. In this device, a precise volume of sample is passed through a concentrator which traps the selected ions. After the sample has passed through, an eluent is passed through the concentrator to elute the ions and deliver them to the chromatograph for analysis.

Chromatographic analysis is a batch type operation where a sample is collected, injected and analyzed, the sample being of controlled volume to assure repeatability from sample to sample. This is necessary for example to determine changes in a process fluid which require adjustments in the process parameters. If samples of different volume are injected, and the analysis results compared, it is likely that the results will not be accurate which could lead to problems in determining the proper process parameters.

One method for providing a constant volume sample is to use a metering pump, such as a gear pump. The pump is operated for a given time period, based on the pumps' expected flow rate, to provide repeatable samples to the chromatograph. However, variations result because of differences in the sample pump suction pressure from sample to sample and also due to the presence of solids in the sample which may restrict or block flow.

In U.S. Pat. No. 3,975,946, a constant volume sampling device is described which utilizes at least two pump means, each of which is operable to supply a finite volume of carrier liquid at a flow rate determined by the rate of an input drive to the pump means. The system described is complex to assemble and operate, and additionally fails to address the problems encountered due to differences in suction pump pressures and/or with solids containing samples.

SUMMARY OF THE INVENTION

It is an object of the present invention to provide a sampling apparatus for a chromatograph that provides constant volume samples.

It is a further object to provide a sampling apparatus for a chromatograph which is immune to the problem of solids in the sample to be analyzed.

It is yet another object to provide a sampling apparatus which is unaffected by changes in the suction head pressure of the pump.

These and other objects of the present invention are achieved by a sample apparatus for a chromatograph comprising sample holding means such as a burette, liquid level sensing means located at a selected height on the sample holding means, transport means for providing liquid to the sample holding means, and switch means connected to the liquid level sensing means and to the transport means such that when the selected liquid level is reached, the switch means halts the flow of liquid through the transport means.

Utilizing this device, the sample is precisely determined, regardless of whether the fluid contains solids. Once the precise sample volume is determined, it can be injected by a pressure pulse, pump, or other means into the analytical device with full confidence that a precise volume is delivered. On an ion chromatograph, the sample apparatus is used to collect the sample as it leaves the concentrator to assure that the precise volume of liquid has passed through the concentrator. Once emptied, a second sensor can be used to begin refilling the sample holding means.

DETAILED DESCRIPTION OF THE INVENTION

Figure 1:
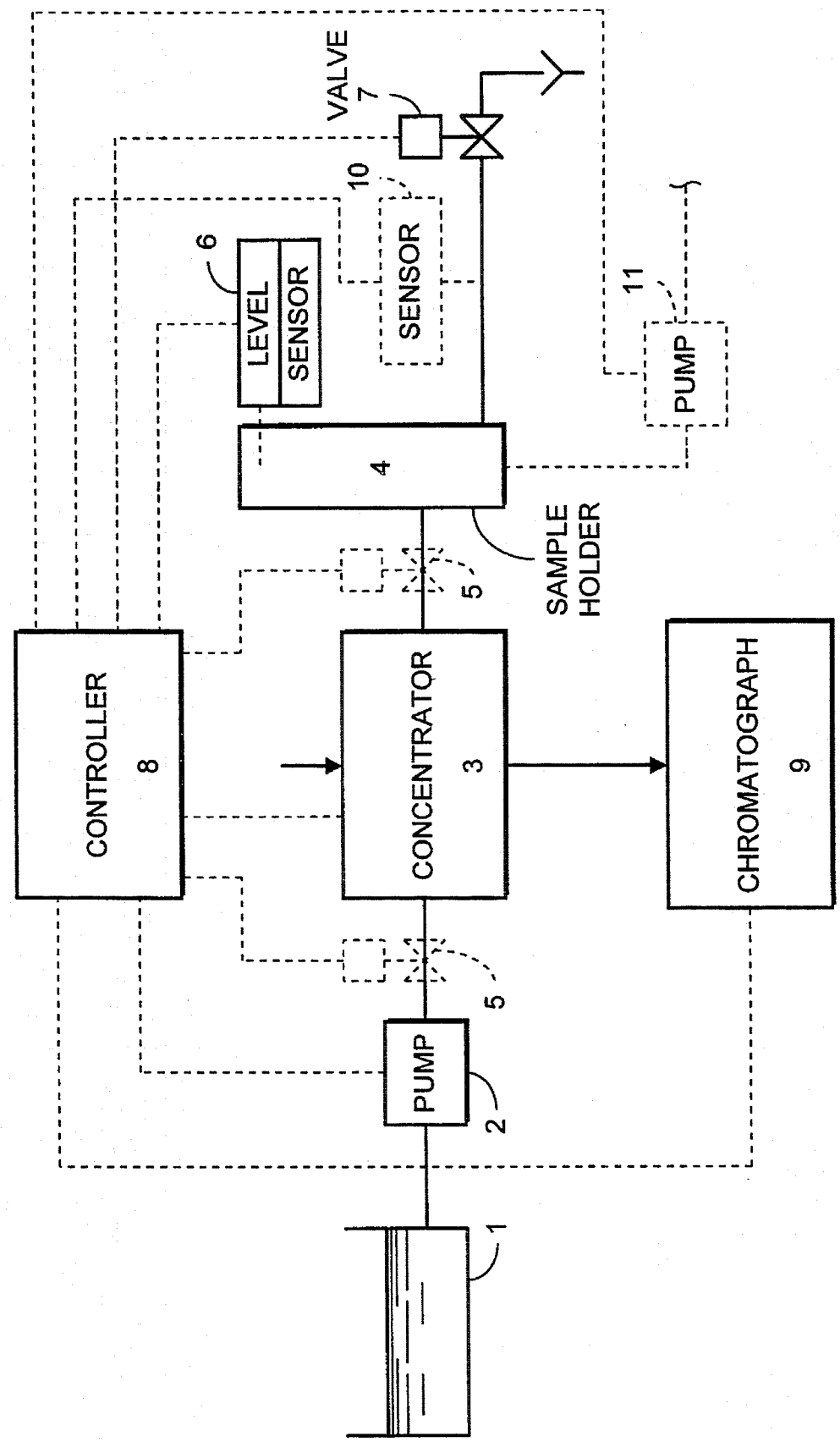
FIG. 1 shows the sample analysis system of the present invention.

Referring to FIG. 1, a block flow and control diagram shows the liquid sample system according to the present invention. The system includes a sample reservoir 1 connected to a pump 2. The sample reservoir may represent a vessel, pipe, or container having a liquid to be sampled. The pump is used to transport the sample from the reservoir through a concentrator 3 to a sample holding means 4. An inlet valve 5 shown in phantom is optionally located between the pump and the concentrator or between the pump and the sample holding means to permit or deny passage of the sample fluid to the sample holding means. An adjustable liquid level sensor 6 is associated with the sample holding means to determine when the correct volume of sample fluid is present in the sample holding means. An outlet valve 7 is provided to prevent fluid from exiting the sample holding means during filling. When the correct volume is reached the sensor 6 communicates with a controller 8 which signals the pump 2 to halt the fluid flow. The controller may also be integrated with a chromatograph 9 such that it signals the concentrator to permit an eluant fluid to flow through the concentrator to the chromatograph.

The sample may be displaced using a pump or pressure device to assure complete transfer of the sample to the sample holding means. An additional sensor 10 shown in phantom can be located near the outlet valve 7 to signal the controller that the sample holding means is empty. An outlet pump 11 may be used alternatively or in addition to the valve 7. The controller may then close the outlet valve 7 and start the pump 2 to refill the sample holding means, to begin another sample cycle. Optionally, the controller could also signal the valve 5 and the outlet pump 11 to start/stop in coordination with the filling operation.

Figure 2:
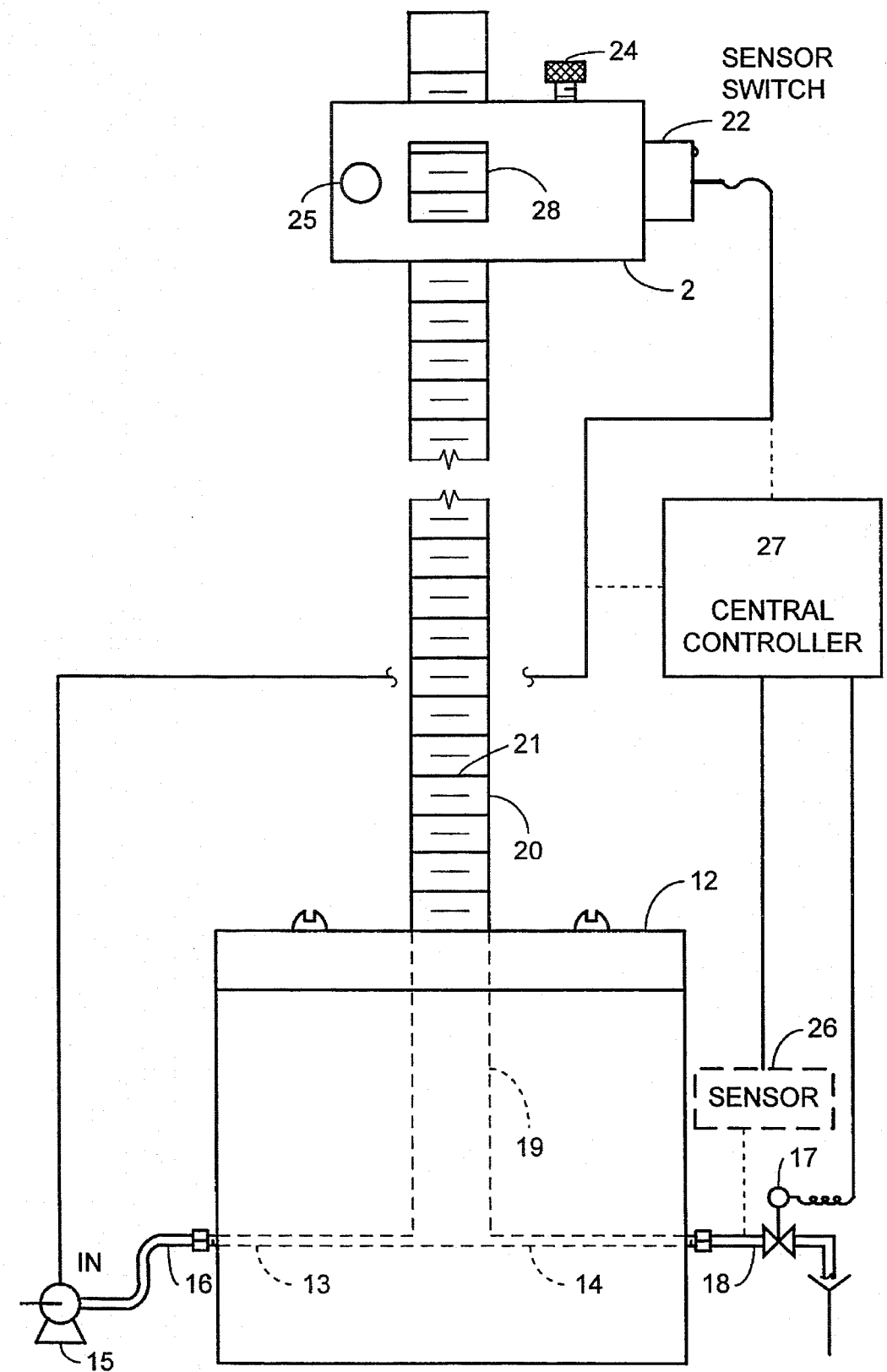
FIG. 2 is an enlarged view of the sample analysis system of FIG. 1.

Referring to FIG. 2, the sample system of the invention utilizes a base 12 having an inlet passage 13 and an outlet passage 14. An inlet pump 15 located in a tube 16 connected to the inlet passage 13. An outlet valve 17 is located in a tube 18 connected to the outlet passage 14. Value 17 may comprise a solenoid valve. The base includes a cylindrical passage 19 for retaining the sample holding means therein. In this instance, a burette 20 having volume gradations 21 serves as the sample holding means and is located in the cylindrical passage 19.

A capacitance type liquid level sensor/switch 22 is located in a housing 23 which is vertically movable over the burette. Screws 24 and 25 allow adjustment of the sensor/switch at a selected location corresponding to the desired volume. The sensor/switch 22 includes sensor means which are responsive to the difference in capacitance between an empty burette and one containing liquid. The sensor activates an internal switching device to provide an on/off signal which may be used to activate the inlet pump 15. Thus, when the proper level is achieved, the inward fluid flow is stopped.

This switch can be used to control both the inlet pump and outlet valve simultaneously. The outlet valve can be solenoid activated and responsive in an on/off manner to an electrical signal, the valve and inlet pump configured such that when the pump is on, the valve is closed, etc.

Optionally, a sensor 26 is located in the outlet tubing 18 to detect that the burette is empty, which signals the outlet valve to close and the inlet pump to begin flow. Thus, the full sample cycle can be automated.

As described previously, a central controller 27 can be used to receive the output signals from the sensors, as well as other signals, such as a signal that the chromatograph is ready to accept a sample, so as to fully integrate the sample system with the analytical device. Virtually any logic controller or computer based controller could be used to coordinate the signals for properly filling the sample holding means. Thus, the controller could communicate with the inlet pump and outlet valve, to hold the sample until such time as the analytical device is ready to accept a sample and then when that signal is received, the controller is used to signal the outlet valve to allow sample discharge and refilling to proceed. In addition, if a pump or other device is used to effect fluid discharge, these devices could be activated/deactivated using the same controller.

Figure 3B:
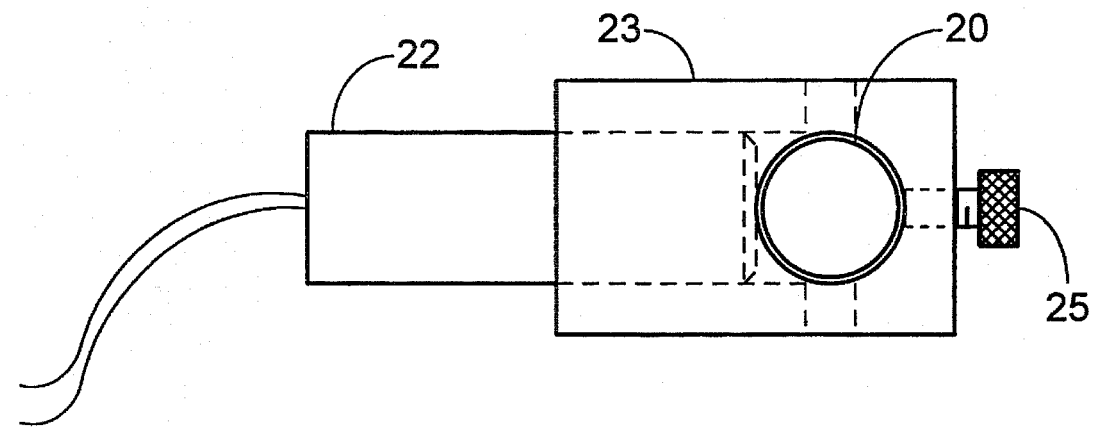
FIG. 3a a cross sectional view of the level sensor holding device of the invention, with FIG. 3b being a top view of the level sensor holding device.
Figure 3A:
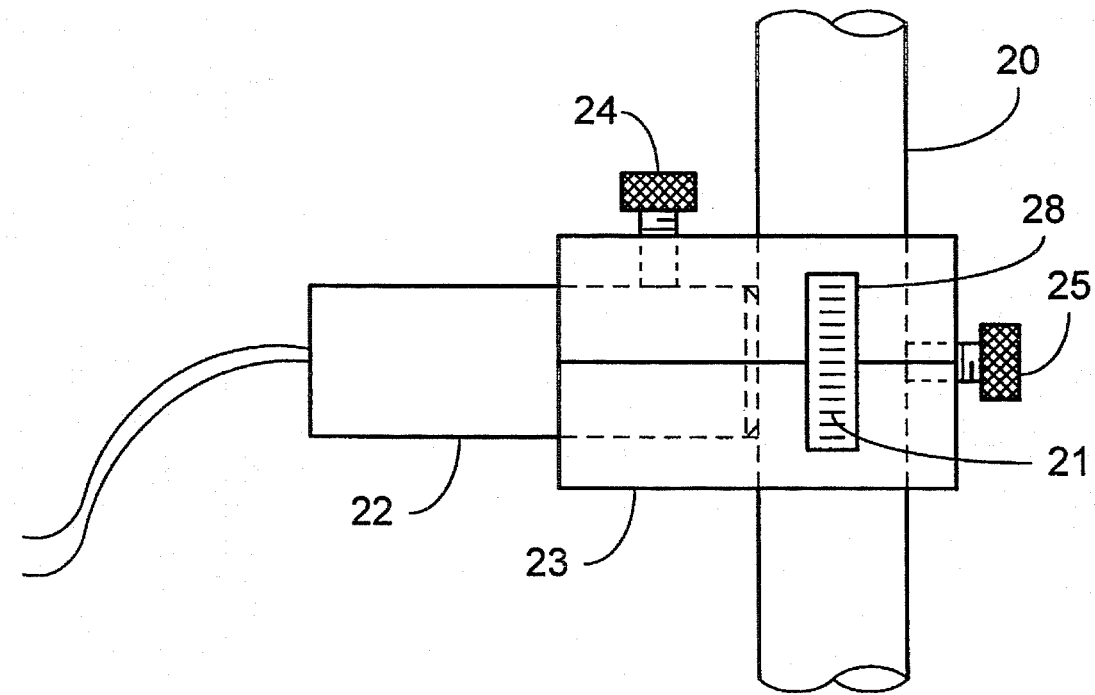

Referring to FIG. 3, an enlarged side view of the housing 23 is shown which includes a window 28 which is alignable with the gradations 21 on the burette. The thumb screw 24 is provided for holding the sensor/switch 22 in the housing and another screw 25 used to hold the device at a particular height relative to the burette gradations. Thus, one can loosen the thumb screw 25, and vertically adjust the position of the liquid level sensor/switch in correspondence to the gradations on the burette and thereby be assured that the proper liquid volume is achieved from sample to sample.

Utilizing the present invention, an accurate determination of sample volume can be achieved from sample to sample, regardless of pump suction pressures or the presence of solids. In each instance, a constant volume sample is achieved and injected for analysis, without complicated apparatus. The simplicity of the system is valuable for assuring analytical reliability from sample to sample.

While preferred embodiments of the present invention have been shown and described, it will be understood by those skilled in the art that various changes or modifications could be made without varying from the scope of the present invention. For example, while a capacitance type level sensor is disclosed, it would be understood that various other non-invasive liquid level sensing means, such as ultrasonic, etc. could be used in the apparatus of the invention. In addition, the sample holding means could be any calibrated vessel of sufficient size to accommodate the expected sample volume and virtually any type of valve or flow controlling means could be used in the inlet and outlet locations with this apparatus to effect precise sample control.

We claim:

1. An ion chromatograph for determining the amount of a selected ion in a sample, the ion chromatograph having a concentrator for capturing the ions therein, the improvement comprising:

calibrated sample holding means, located adjacent to the concentrator for collecting a sample therefrom, liquid level sensing means located at a selected height on the sample holding means, transport means for providing liquid from the concentrator to the sample means, switch means connected to the liquid level sensing means and to the transport means such that when the selected liquid level is reached, the sensing means sends a signal to the switch means to halt the flow of liquid through the concentrator to the sample holding means.

2. The ion chromatograph of claim 1 wherein the transport means comprises signal activated pump means, responsive to the switch means, for controlling the flow of liquid to the sample holding means.

3. The ion chromatograph of claim 1 wherein the sample holding means comprises a burette.

4. The ion chromatograph of claim 1 wherein the liquid level sensing means comprises a capacitance sensor.

5. The ion chromatograph of claim 1, further comprising a controller for accepting the signal from the liquid level sensing means and for communicating with the transport means for effecting cyclic filling and emptying of the sample holding means.

6. The ion chromatograph of claim 1, further comprising second transport means for discharging liquid from the sample holding means, the second transport means connected to the switch means such that the switch means, after halting the flow of liquid to the sample holding means, effects discharge of the liquid from the sample holding means through the second transport means.

7. The ion chromatograph of claim 1 wherein the transport means comprise signal activated valve means, responsive to the switch means, for controlling the flow of liquid to the sample holding means.

8. The ion chromatograph of claim 6 wherein the second transport means comprise a signal activated valve located in a discharge tube of the sample holding means.

9. The ion chromatograph of claim 6 wherein the second transport means comprise a signal activated pump.

10. The ion chromatograph of claim 6 further comprising sensor means associated with the second transport means, the sensor means communicating with the switch means so as to provide a signal indicating that the sample holding means are empty.

11. A method for providing precise volumetric samples in an ion chromatograph device comprising:

providing a sample apparatus having calibrated sample holding means, located adjacent to a concentrator, for collecting the sample therefrom, locating a liquid level sensing means at a selected height on the sample holding means, providing liquid from the concentrator to the sample holding means using transport means, providing switch means connected to the liquid level sensing means and to the transport means such that when the selected liquid level is reached, the sensor means sends a signal to the switch means to halt the flow of liquid from the concentrator to the sample holding means.

* * * * *